US010159758B2

United States Patent
Jang et al.

(10) Patent No.: US 10,159,758 B2
(45) Date of Patent: Dec. 25, 2018

(54) CORE/DOUBLE SHELL STRUCTURED RED LIGHT-EMITTING UPCONVERSION NANOPHOSPHORS

(71) Applicant: KOREA INSTITUTE OF SCIENCE AND TECHNOLOGY, Seoul (KR)

(72) Inventors: Ho Seong Jang, Seoul (KR); So Hye Cho, Seoul (KR); Seung Yong Lee, Seoul (KR); A Ra Hong, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 15/871,062

(22) Filed: Jan. 15, 2018

(65) Prior Publication Data

US 2018/0303959 A1    Oct. 25, 2018

(30) Foreign Application Priority Data

Apr. 21, 2017    (KR) .......................... 10-2017-0051588

(51) Int. Cl.
| | |
|---|---|
| *A61K 9/00* | (2006.01) |
| *A61K 49/00* | (2006.01) |
| *C09K 11/77* | (2006.01) |
| *G01N 21/64* | (2006.01) |
| *B82Y 5/00* | (2011.01) |
| *H01G 9/20* | (2006.01) |

(52) U.S. Cl.
CPC ...... *A61K 49/0093* (2013.01); *A61K 49/0019* (2013.01); *B82Y 5/00* (2013.01); *C09K 11/7766* (2013.01); *G01N 21/6428* (2013.01); *H01G 9/2059* (2013.01); *C01P 2004/64* (2013.01)

(58) Field of Classification Search
CPC .................................................. A61K 49/0093
See application file for complete search history.

(56) References Cited

U.S. PATENT DOCUMENTS

2016/0122635 A1 *    5/2016   Liu ................... C09K 11/7704
                                                             250/473.1

OTHER PUBLICATIONS

A. Skripka et al., "Covering the optical spectrum through collective rare-earth doping of NaGdF4 nanoparticles: 806 and 980nm excitation routes," Phys.Chem. Chem. Phys., Apr. 4, 2017, pp. 11825-11834, vol. 19.

(Continued)

*Primary Examiner* — Paul W Dickinson
(74) *Attorney, Agent, or Firm* — Cantor Colburn LLP

(57) ABSTRACT

Provided is a nanophosphor having a core/double shell structure, the nanophosphor including a upconversion core including a $Yb^{3+}$, $Ho^{3+}$, and $Ce^{3+-}$ co-doped fluoride-based nanophosphor represented by Formula 1; a first shell surrounding at least a portion of the upconversion core, and comprising a $Nd^{3+}$ and $Yb^{3+}$ co-doped fluoride-based crystalline composition represented by Formula 2; and a second shell surrounding at least a portion of the first shell, and having paramagnetic properties represented by Formula 3.

9 Claims, 11 Drawing Sheets

(56) References Cited

OTHER PUBLICATIONS

Daqin Chen et al., "Nd3+-Sensitized Ho3+ Single-Band Red Upconversion Luminescence in Core-Shell Vanoarchitecture," The Journal of Physical Chemistry Letters, Jul. 2, 2015, pp. 2833-2840, vol. 6, American Chemical Society.

Korean Office Action for corresponding Korean Patent Application No. 10-2017-0051588 dated Aug. 7, 2018, citing the above references. In conformance with MPEP 609—Concise explanation of the relevance includes issue date of KR OA and reference cited therin.

* cited by examiner

CORE/DOUBLE SHELL STRUCTURED RED LIGHT-EMITTING UPCONVERSION NANOPHOSPHORS

CROSS-REFERENCE TO RELATED APPLICATION

This application claims the benefit of Korean Patent Application No. 10-2017-0051588, filed on Apr. 21, 2017, in the Korean Intellectual Property Office, the disclosure of which is incorporated herein in its entirety by reference.

BACKGROUND

1. Field

The present disclosure relates to an upconversion nanophosphor that emits red light by using invisible near infrared light as an excitation source for being applicable as a fluorescent contrast agent and a contrast agent for magnetic resonance imaging. More particularly, the present disclosure relates to a red light-emitting upconversion nanophosphor with a high efficiency core/shell/shell structure capable of converting near-infrared light having a wavelength of about 980 nm and about 800 nm into visible light.

2. Description of the Related Art

Upconversion nanophosphors refer to a phosphor having a size of less than 100 nm which emits visible light having an energy greater than that externally applied. In general, Yb, as a sensitizer, and Er and Tm, as an activator, are doped into an inorganic host, so that they are excited by infrared light having a wavelength of about 980 nm to emit green light and blue light. [Chem. Rev. vol. 104, 139-174 (2004)]. Generally, when fluorescence imaging is performed on cells or animals, organic dyes are used in large amounts. The organic dyes used in this case exhibit down conversion luminescence in which visible light having a wavelength longer than an excitation wavelength is emitted. Therefore, ultraviolet light or visible light, each having a short wavelength, is used as an excitation light source. However, when infrared light is used as the excitation light, biomolecules may be less damaged, and infrared light may infiltrate deeply into tissues. Accordingly, when upconversion nanophosphors, which are excited by infrared light to emit visible light, are used as a fluorescent contrast agent, more advantages may be obtained than when organic dyes are used as a contrast agent. In particular, since upconversion nanophosphors have high upconversion efficiency, unlike organic dyes or quantum dots that emit visible light by two-photon adsorption, they can use relatively inexpensive diode laser as an excitation light source and is thus suitable for use as a fluorescent contrast agent. Thus, there are many studies to use upconversion nanophosphors as a fluorescent contrast agent. In particular, there is a report that when $NaYF_4$ doped with Yb and Er is excited by a 980 nm infrared light laser, strong green luminescence may occur, and cell imaging and animal imaging results are obtained by using $NaYF_4$:Yb, Er nanophosphors. [Biomaterials vol. 30, 5592-5600 (2009)]. However, although the 980 nm infrared light used as the excitation light of the upconversion nanophosphor may infiltrate deeper into tissues and may cause less damage on biomolecules than ultraviolet light or visible light, the absorption peak of the water molecule appears in this wavelength range. Accordingly, when a 980 nm laser is irradiated to a cell or tissue, the temperature of the cell or tissue is raised. This issue may be addressed by using Nd as a sensitizer. In this case, infrared light having a wavelength of about 800 nm is used as an excitation light source instead of infrared light having a wavelength of 980 nm. However, since Nd, which is a sensitizer, is doped into a host together with Er or Tm, which is an activator, the activator luminescence intensity may be greatly reduced, the Liu group and the Yan group introduced a core/shell structure to produce upconversion nanophosphors that exhibit bright green and blue luminescence when excited with infrared light having a wavelength of 800 nm. [J. Am. Chem. Soc. vol. 135, 12608-12611 (2012), ACS Nano vol. 7, 7200-7206 (2012)] Although upconversion nanophosphors emit visible light due to the infrared light, which infiltrates deep into living tissues, since the emitted light is green or blue visible light, the tissue-infiltrating efficiency of the emitted light is poor. Therefore, if an upconversion nanophosphor that is excited by an infrared light having a wavelength of 800 nm and emits light with a low absorption rate in tissues is developed, the efficiency of in vivo imaging can be increased. In addition, when magnetic resonance imaging effects are obtained as well as upconversion imaging characteristics, the imaging accuracy of the desired target can be increased.

SUMMARY

Provided is an upconversion nanophosphor capable of converting infrared light having a wavelength of an 800 nm into red light having a low absorption rate with respect to living tissues, wherein when excited by near infrared light having a wavelength of 800 nm, the upconversion nanophosphor obtains a magnetic resonance imaging effect as well as the strong red luminance. However, these objectives are an example only and do not limit the scope of the present disclosure.

Additional aspects will be set forth in part in the description which follows and, in part, will be apparent from the description, or may be learned by practice of the presented embodiments.

The above objectives may be attained by the following features of the present disclosure.

According to an aspect of an embodiment, a core/double shell structured red light-emitting upconversion nanophosphor is provided. The core/double shell structured red light-emitting upconversion nanophosphor may include a fluoride-based nanoparticle core doped with $Yb^{3+}$, $Ho^{3+}$, and $Ce^{3+}$ represented by Formula 1.

$$NaGd_{1-x-y-z-w}L_wF_4:Yb^{3+}{}_x,Ho^{3+}{}_y,Ce^{3+}{}_z. \quad \text{[Formula 1]}$$

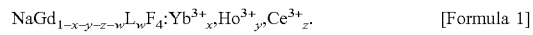

In Formula 1, x is a real number and satisfies the condition of $0 \leq x \leq 0.5$, y is a real number and satisfies the condition of $0 < y \leq 0.3$, and z is a real number and satisfies the condition of $0 \leq z \leq 0.5$ (excluding a case in which each of x, y, and z is 0 at the same time). In this regard, x, y, and z satisfy the condition of $0 < x+y+z \leq 1$, L is any one selected from Y, La, Tb, Dy, Er, Tm, Nd, Lu, and a combination thereof, and w is a real number and satisfies the conditions of $0 \leq w \leq 1$ and $0 < x+y+z+1$.

$Ho^{3+}$ in Formula 1 acts as an activator. Therefore, when y is 0, the upconversion nanophosphor does not undergo upconversion, which has been confirmed. Accordingly, excluded is the case in which y in Formula 1 is 0.

There is a case in which, in Formula 1, each of x, y, and z is not 0 at the same time and w is not 0. In this case, when the sum of x, y, z, and w is a real number and satisfies the condition of $0 < x+y+z+w < 1$, Formula 1 may be $NaGd_{1-x-y-z-w}L_wF_4:Yb^{3+}_x,Ho^{3+}_y,Ce^{3+}_z$; and when x+y+z+w=1, Formula 1 may be $NaL_wF_4:Yb^{3+}_x,Ho^{3+}_y,Ce^{3+}_z$.

There is a case in which, in Formula 1, x is 0, each of y and z is not 0 at the same time, and w is not 0. In this case, when the sum of y, z, and w is a real number and satisfies the condition of 0<y+z+w<1, Formula 1 may be $NaGd_{1-y-z-w}L_wF_4:Ho^{3+}_y,Ce^{3+}_z$; and when x+y+z+w=1, Formula 1 may be $NaL_wF_4:Ho^{3+}_y,Ce^{3+}_z$.

There is a case in which, in Formula 1, z is 0, each of x and y is not 0 at the same time, and w is not 0. In this case, when the sum of x, y, and w is a real number and satisfies the condition of 0<x+y+w<1, Formula 1 may be $NaGd_{1-x-y-w}L_wF_4:Yb^{3+}_x,Ho^{3+}_y$; and when x+y+w=1, Formula 1 may be $NaL_wF_4:Yb^{3+}_x,Ho^{3+}_y$.

There is a case in which, in Formula 1, each of z and x is 0 at the same time, y is not 0, and w is not 0. In this case, when the sum of y and w is a real number and satisfies the condition of 0<y+w<1, Formula 1 may be $NaGd_{1-y-w}L_wF_4:Ho^{3+}_y$; and when y+w=1, Formula 1 may be $NaL_wF_4:Ho^{3+}_y$. However, each of $Yb^{3+}$ and $Ce^{3+}$ in Formula 1 acts as a sensitizer. Accordingly, when each of z and x is 0 at the same time, the nanophosphor may have weak red luminance. This case has been confirmed. Accordingly, any one of x and z in Formula 1 may not be 0.

There is a case in which, in Formula 1, z is 0, each of x and y is not 0, and w is 0. In this case, when the sum of x and y is a real number and satisfies the condition of 0<x+y<1, Formula 1 may be $NaGd_{1-x-y}F_4:F_4:Yb^{3+}_x,Ho^{3+}_y$.

The nanophosphor may include a core including the nanoparticle and a first shell located on a surface of the core, and the first shell may include a compound represented by Formula 2 below.

$NaY_{1-p-q-r}M_rF_4:Nd^{3+}_p,Yb^{3+}_q$ [Formula 2]

In Formula 2, p is a real number and satisfies the condition of 0<p≤1, q is a real number and satisfies the condition of 0≤q≤0.5, M is any one selected from first rare-earth elements and a combination thereof, the first rare-earth elements may be selected from La, Ce, Gd, Pr, Sm, Eu, Tb, Dy, Ho, Er, and Lu, and r is a real number and satisfies the condition of 0≤r≤1. In this regard, r satisfies the condition of 0<p+q+r≤1.

When Formula 2 does not include $Nd^{3+}$, the nanophosphor does not absorb near infrared light having a wavelength of about 800 nm, which has been confirmed. Accordingly, excluded is a case in which p in Formula 2 is 0.

In one embodiment, r in Formula 2 is 0. In this case, Formula 2 may be $NaY_{1-p-q}F_4:Nd^{3+}_p,Yb^{3+}_q$. In one embodiment, each of r and q is 0 at the same time. In this case, Formula 2 may be $NaY_{1-p}F_4:Nd^{3+}_p$.

In one embodiment, the sum of p, q, and r in Formula 2 is 1. In this case, Formula 2 may be $NaM_rF_4:Nd^{3+}_p,Yb^{3+}_q$. In one embodiment, the sum of p, q, and r is 1 and q is 0. In this case, Formula 2 may be $NaM_rF_4:Nd^{3+}_p$.

The nanophosphor includes the core and the first shell, and may have an emission peak in a red region since $Nd^{3+}$ ion, which is a co-sensitizer, absorbs infrared light and $Yb^{3+}$ ion transfers absorbed energy to $Ho^{3+}$ ion.

The nanophosphor may include the structure of the nanoparticle-containing core/shell, and a second shell located on a surface of the structure of the nanoparticle-containing core/shell, and the second shell may include a compound represented by Formula 3 below.

$NaGd_{1-s}N_sF_4$ [Formula 3]

s in Formula 3 is a real number and satisfies the condition of 0≤s≤1, and N may be any one selected from rare-earth elements and a combination thereof. The rare earth elements may be selected from Y, La, Ce, Nd, Pr, Sm, Eu, Tb, Dy, Ho, Yb, Er, and Lu.

When s in Formula 3 is 0, Formula 3 may be $NaNF_4$. In this case, the core/double shell structured red light-emitting upconversion nanophosphor may be used as a contrast agent for magnetic resonance imaging.

When s in Formula 3 is 1, Formula 3 may be $NaNF_4$. In this case, the core/double shell structured red light-emitting upconversion nanophosphor may be used as a fluorescent contrast agent.

The core of the core/double shell structured red light-emitting upconversion nanophosphor may have a size of about 1 nm to about 20 nm.

The core/double shell structured red light-emitting upconversion nanophosphor may have a size of about 3 nm to about 100 nm, for example, about 3 nm to about 50 nm.

The nanophosphor having the core/double shell structure may absorb near infrared light having a wavelength of about 770 nm to about 870 nm and show red light luminescent characteristics.

The nanophosphor having the core/double shell structure may absorb near infrared light having a wavelength of about 940 nm to about 1000 nm and show red light luminescent characteristics.

According to an aspect of another embodiment, a fluorescent contrast agent is provided. The fluorescent contrast agent includes the core/double shell structured red light-emitting upconversion nanophosphor.

According to an aspect of another embodiment, a contrast agent for magnetic resonance imaging is provided. The contrast agent for magnetic resonance imaging includes the core/double shell structured red light-emitting upconversion nanophosphor.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
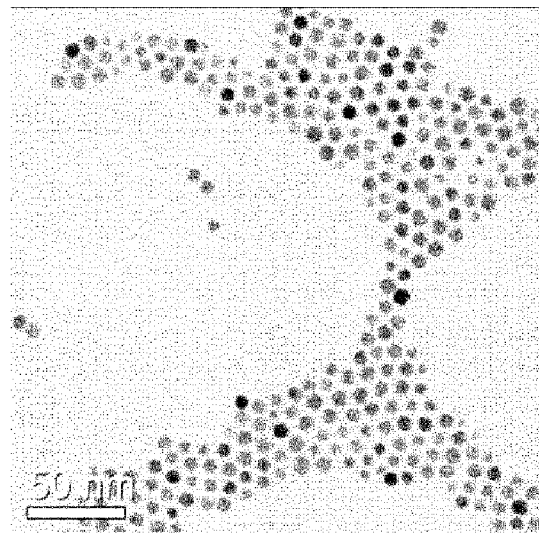
FIG. 1 shows a transmission electron microscopy (TEM) image of a core upconversion nanophosphor according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects.

Hereinafter, an upconversion nanophosphor according to an embodiment of the present disclosure will be described with reference to the accompanying drawings. The specific composition of the upconversion nanophosphor is described in the summary section of the present application. An upconversion nanophosphor according to the present disclosure is a nanoparticle with a core/shell/shell structure that absorbs near infrared light having a wavelength of 800 nm, and exhibits strong red luminescence and has a magnetic resonance imaging effect. However, the present disclosure is not limited to embodiments, and other embodiments may be easily provided by, for example, adding or replacing components.

However, the embodiments of the present disclosures described above and shown in the drawings should not be construed as limiting the technical concept of the present disclosure, and embodiments of the present disclosures are provided to more fully describe the present disclosure.

Hereinafter, specific examples of a method of producing an upconversion nanophosphor having a core/shell/shell structure according to embodiments of the present disclosures will be described.

<Example 1> Preparation of $Yb^{3+}$ and $Ho^{3+}$-Coated Upconversion Core Nanophosphor 0.8 mmol gadolinium chloride hexahydrate ($GdCl_3.6H_2O$), 0.18 mmol ytterbium chloride hexahydrate ($YbCl_3.6H_2O$), 0.02 mmol holmium chloride hexahydrate ($HoCl_3.6H_2O$), and 3.1 mmol sodium oleate ($C_{18}H_{33}O_2Na$) were weighed, and a mixed solvent including a predetermined amount of water, ethanol, and hexane was added thereto, and the resultant mixture was heat treated at a temperature of 70° C. to form a lanthanide complex (Formation of a complex). The lanthanide complex was mixed with a solution containing oleic acid and 1-octadecene and heat-treated at 150° C. for 30 minutes to prepare a first mixed solution containing the lanthanide complex (preparation of a first mixed solution).

10 ml of a methanol solution containing 2.5 mmol of sodium hydroxide and 4 mmol of ammonium fluoride was prepared (preparation of a second mixed solution), and then, the second mixed solution was mixed with the first mixed solution containing the lanthanide complex (preparation of a reaction solution).

After the mixing is sufficiently performed, methanol was removed therefrom and the resultant solution was heat treated in an inert gas atmosphere. At this time, when the heat treatment temperature is lower than 250° C., a single hexagonal-phase nanocrystal is not completely formed and a phosphor does not exhibit strong luminescence. When the heat treatment temperature is higher than 370° C., aggregation of particles occurs due to excessive reaction, resulting in a very large particle size, a non-uniform distribution of the size, and a weak luminescence. Therefore, the heat treatment temperature may be in a range of about 250° C. to about 370° C. and the heat treatment time may be in a range of about 10 minutes to about 4 hours (preparation of nanoparticles). The resultant nanoparticles were cooled to room temperature after the heat treatment process, thereby obtaining a colloidal nanophosphor with a diameter of about 1 nm to about 20 nm. The prepared nanophosphor was washed with acetone or ethanol, and then, stored while being dispersed in a non-polar solvent such as hexane, toluene, or chloroform.

Figure 2:
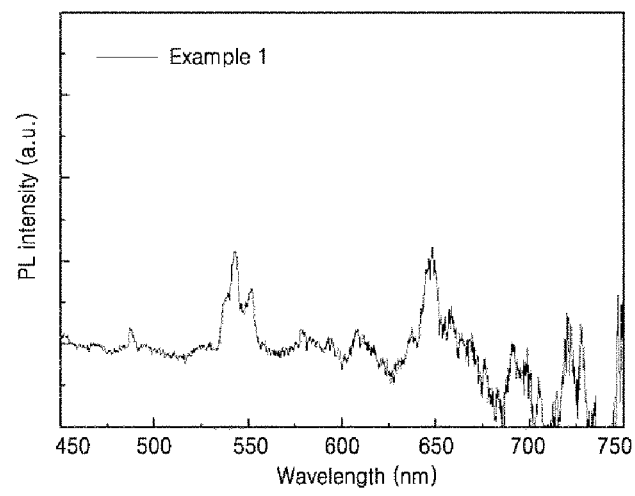
FIG. 2 shows a luminescence spectrum of a core upconversion nanophosphor according to an embodiment of the present disclosure, when excited by infrared light having a wavelength of 980 nm.

FIG. 1 shows a transmission electron microscopy (TEM) image of the core upconversion nanophosphor according to Example 1, and FIG. 2 shows absorption and photoluminescence (PL) spectra of the core upconversion nanophosphor according to Example 1. Referring to the TEM image of FIG. 1, it is seen that the core upconversion nanophosphor has a uniform size of less than 20 nm. Referring to the absorption and PL spectra of FIG. 2, the absorption peak appears in the 980 nm infrared light region, and a strong luminescence peak appears in the 550 nm green region.

<Example 2> Preparation of $Yb^{3+}$, $Ho^{3+}$ and $Ce^{3+}$-Coated Upconversion Core Nanophosphor 0.5 mmol gadolinium chloride hexahydrate ($GdCl_3.6H_2O$), 0.18 mmol ytterbium chloride hexahydrate ($YbCl_3.6H_2O$), 0.02 mmol holmium chloride hexahydrate (HoCl$_3$.6H$_2$O), 0.3 mmol cerium chloride heptahydrate (CeCl$_3$.7H$_2$O), and 3.1 mmol sodium oleate (C$_{18}$H$_{33}$O$_2$Na) were weighed, and a mixed solvent including a predetermined amount of water, ethanol, and hexane was added thereto, and the resultant mixture was heat treated at a temperature of 70° C. to form a lanthanide complex (Formation of a complex). The lanthanide complex was mixed with a solution containing oleic acid and 1-octadecene and heat-treated at 150° C. for 30 minutes to prepare a first mixed solution containing the lanthanide complex (preparation of a first mixed solution).

10 ml of a methanol solution containing 2.5 mmol of sodium hydroxide and 4 mmol of ammonium fluoride was prepared (preparation of second mixed solution), and then, the second mixed solution was mixed with the first mixed solution containing the lanthanide complex (preparation of a reaction solution).

After the mixing is sufficiently performed, methanol was removed therefrom and the resultant solution was heat treated in an inert gas atmosphere. At this time, when the heat treatment temperature is lower than 250° C., a single hexagonal-phase nanocrystal is not completely formed and a phosphor does not exhibit strong luminescence. When the heat treatment temperature is higher than 370° C., aggregation of particles occurs due to excessive reaction, resulting in a very large particle size, a non-uniform distribution of the size, and a weak luminescence. Therefore, the heat treatment temperature may be in a range of about 250° C. to about 370° C. and the heat treatment time may be in a range of about 10 minutes to about 4 hours (preparation of nanoparticles). The resultant nanoparticles were cooled to room temperature after the heat treatment process, thereby obtaining a colloidal nanophosphor with a diameter of about 1 nm to about 20 nm. The prepared nanophosphor was washed with acetone or ethanol, and then, stored while being dispersed in a non-polar solvent such as hexane, toluene, or chloroform.

Figure 3:
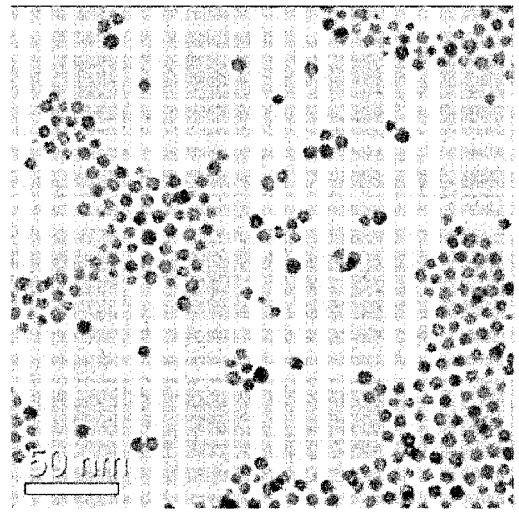
FIG. 3 shows a TEM image of a core upconversion nanophosphor according to an embodiment of the present disclosure.
Figure 4:
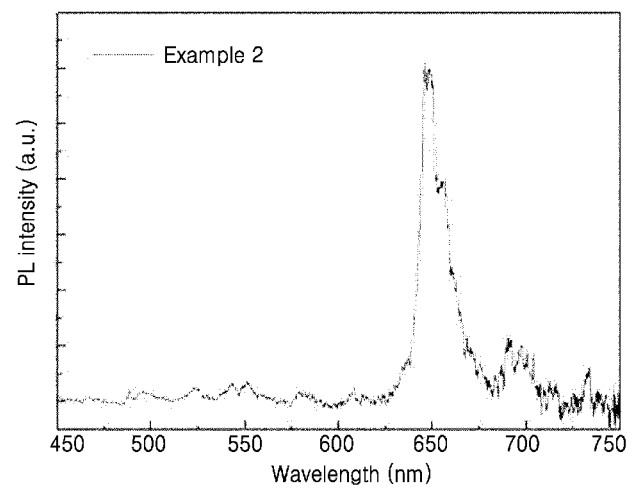
FIG. 4 shows a photoluminescence (PL) spectrum of a core upconversion nanophosphor according to an embodiment of the present disclosure, when excited by infrared light having a wavelength of 980 nm.

FIG. 3 shows a TEM image of the core upconversion nanophosphor according to Example 2, and FIG. 4 shows absorption and PL spectra of the core upconversion nanophosphor according to Example 2. Referring to the TEM image of FIG. 3, it is seen that the core upconversion nanophosphor has a uniform size of less than 20 nm. Referring to the absorption and PL spectra of FIG. 4, the absorption peak appears in the 980 nm infrared light region, and a strong luminescence peak appears in the 650 nm red region.

<Example 3> Synthesis of Nd$^{3+}$ Doped Core/Shell Structured Green Light-Emitting Upconversion Nanophosphor Prepared was a core/shell structured nanophosphor including NaGd$_{0.8}$F$_4$:Yb$^{3+}_{0.18}$, Ho$^{3+}_{0.02}$ nanoparticle prepared according to Example 1 as a core and a Nd$^{3+}$ and Yb$^{3+-}$doped NaYF$_4$ fluoride-based compound as a shell.

0.45 mmol yttrium chloride hexahydrate (YCl$_3$.6H$_2$O), 0.5 mmol neodymium chloride hexahydrate (NdCl$_3$.6H$_2$O), and 0.05 mmol ytterbium chloride hexahydrate (YbCl$_3$.6H$_2$O) were mixed with a solution including oleic acid and 1-octadecene, and the mixture was heat treated at a temperature of 150° C. for 30 minutes to prepare a first mixed solution containing a lanthanide complex (Preparation of first mixed solution).

The first mixed solution was mixed with a solution including NaGd$_{0.8}$F$_4$:Yb$^{3+}_{0.18}$,Ho$^{3+}_{0.02}$ nanoparticle prepared according to Example 1 to prepare a second mixed solution.

10 ml of a methanol solution containing 2.5 mmol of sodium hydroxide and 4 mmol of ammonium fluoride was prepared (preparation of a third mixed solution), and then, the second mixed solution was mixed with a second-mixed solution containing a lanthanide complex (preparation of a reaction solution).

After the mixing is sufficiently performed, methanol was removed therefrom and the resultant solution was heat treated in an inert gas atmosphere. At this time, when the heat treatment temperature is lower than 200° C., a single hexagonal-phase nanocrystal is not completely formed and a phosphor does not exhibit strong luminescence. When the heat treatment temperature is higher than 370° C., aggregation of particles occurs due to excessive reaction, resulting in a very large particle size, a non-uniform distribution of the size, and a weak luminescence. Therefore, the heat treatment temperature may be in a range of about 200° C. to about 370° C. and the heat treatment time may be in a range of about 10 minutes to about 4 hours (preparation of nanoparticles). The resultant nanoparticles were cooled to room temperature after the heat treatment process, thereby obtaining a colloidal nanophosphor with a diameter of about 2 nm to about 60 nm. The prepared nanophosphor was washed with acetone or ethanol, and then, stored while being dispersed in a non-polar solvent such as hexane, toluene, or chloroform.

Figure 5:
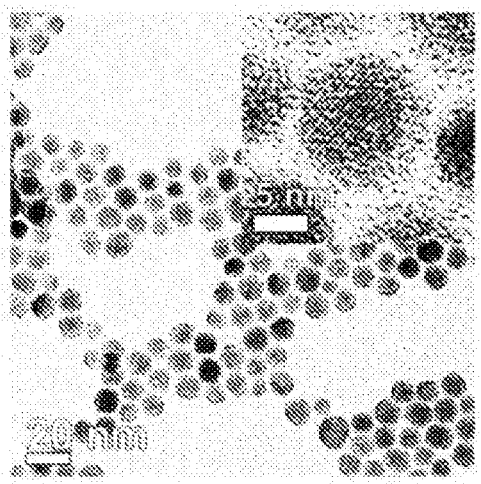
FIG. 5 shows a TEM image of a core/shell structured upconversion nanophosphor according to an embodiment of the present disclosure.
Figure 6:
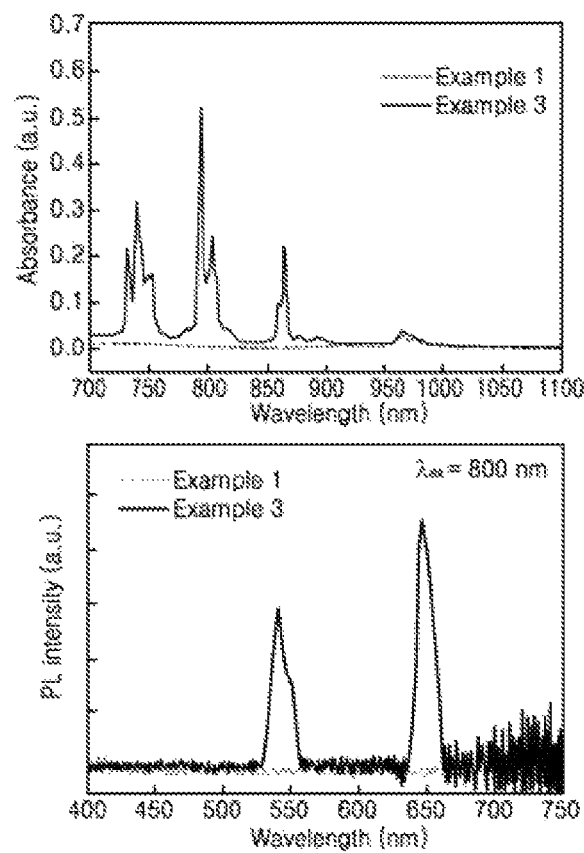
FIG. 6 shows absorption spectra of an upconversion nanophosphor having a core structure and a core/shell structured upconversion nanophosphor according to an embodiment of the present disclosure and a PL spectra thereof when the upconversion nanophosphors are excited at a wavelength of 800 nm.

FIG. 5 shows a TEM image of the core/shell structured upconversion nanophosphor according to Example 3. Referring to the transmission electron micrographic image of the upconversion nanophosphor, it is seen that NaYF$_4$:Nd,Yb shell was formed around the core, thereby resulting in an increase in the size of a nanoparticle. Referring to a high-resolution TEM image thereof, it is seen that the synthesized upconversion nanophosphor having the core/shell structure has a hexagonal structure. Referring to the PL spectra of the upconversion nanophosphor having the core structure synthesized according Example 1 and the upconversion nanophosphor having the core/shell structure synthesized according Example 3 shown in FIG. 6, it is seen that when excited by infrared light having a wavelength of 800 nm, the core upconversion nanophosphor did not have an emission peak, and the core/shell structured upconversion nanophosphor had emission peaks. These results show that the Nd$^{3+}$ doped shell was formed around the core.

<Example 4> Synthesis of Nd$^{3+}$ Doped Core/Shell Structured Red Light-Emitting Upconversion Nanophosphor Prepared was a core/shell structured nanophosphor including NaGd$_{0.5}$F$_4$:Yb$^{3+}_{0.18}$,Ho$^{3+}_{0.02}$,Ce$^{3+}_{0.3}$ nanoparticle prepared according to Example 2 as a core and a Nd$^{3+}$ and Yb$^{3+-}$doped NaYF$_4$ fluoride-based compound as a shell.

0.45 mmol yttrium chloride hexahydrate (YCl$_3$.6H$_2$O), 0.5 mmol neodymium chloride hexahydrate (NdCl$_3$.6H$_2$O), and 0.05 mmol ytterbium chloride hexahydrate (YbCl$_3$.6H$_2$O) were mixed with a solution including oleic acid and 1-octadecene, and the mixture was heat treated at a temperature of 150° C. for 30 minutes to prepare a first mixed solution containing a lanthanide complex (preparation of first mixed solution).

The first mixed solution was mixed with a solution including NaGd$_{0.5}$F$_4$:Yb$^{3+}$$_{0.18}$,Ho$^{3+}$$_{0.02}$,Ce$^{3+}$$_{0.3}$ nanoparticle prepared according to Example 2 to prepare a second mixed solution.

10 ml of a methanol solution containing 2.5 mmol of sodium hydroxide and 4 mmol of ammonium fluoride was prepared (preparation of third mixed solution), and then, the third mixed solution was mixed with the second mixed solution containing a lanthanide complex (preparation of a reaction solution).

After the mixing is sufficiently performed, methanol was removed therefrom and the resultant solution was heat treated in an inert gas atmosphere. At this time, when the heat treatment temperature is lower than 200° C., a single hexagonal-phase nanocrystal is not completely formed and a phosphor does not exhibit strong luminescence. When the heat treatment temperature is higher than 370° C., aggregation of particles occurs due to excessive reaction, resulting in a very large particle size, a non-uniform distribution of the size, and a weak luminescence. Therefore, the heat treatment temperature may be in a range of about 200° C. to about 370° C. and the heat treatment time may be in a range of about 10 minutes to about 4 hours (preparation of nanoparticles). The resultant nanoparticles were cooled to room temperature after the heat treatment process, thereby obtaining a colloidal nanophosphor with a diameter of about 2 nm to about 60 nm. The prepared nanophosphor was washed with acetone or ethanol, and then, stored while being dispersed in a non-polar solvent such as hexane, toluene, or chloroform.

Figure 7:
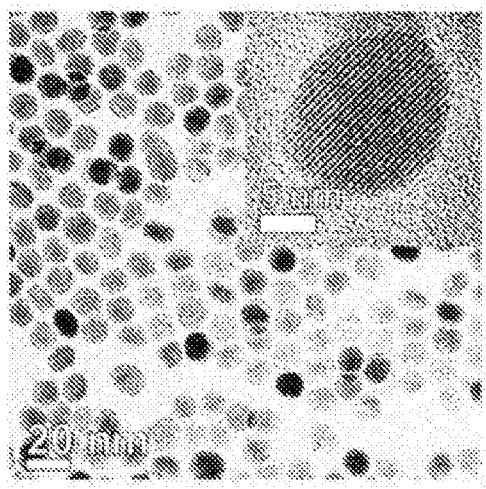
FIG. 7 shows a TEM image of a core/shell structured upconversion nanophosphor according to an embodiment of the present disclosure.
Figure 8:
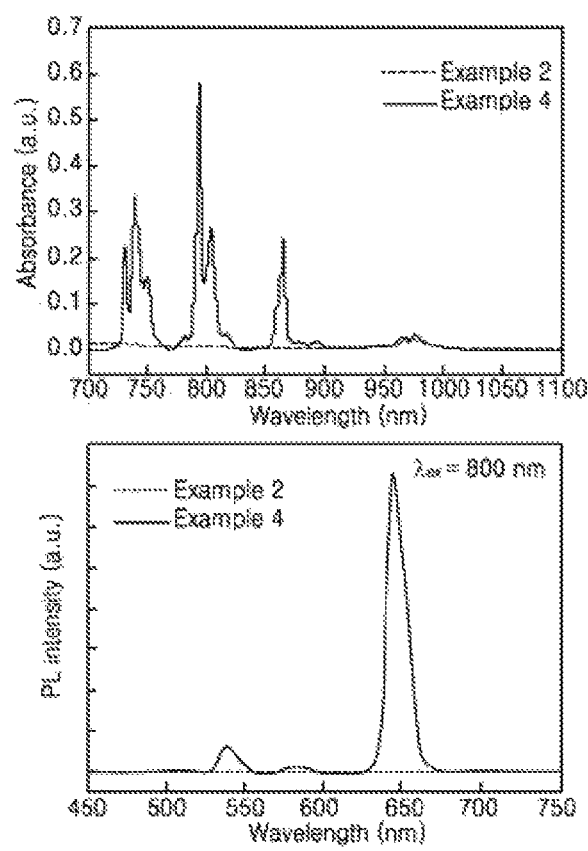
FIG. 8 shows absorption spectra of an upconversion nanophosphor having a core structure and an upconversion nanophosphor having a core/shell structure according to an embodiment of the present disclosure and PL spectra thereof when the upconversion nanophosphors are excited at a wavelength of 800 nm.

FIG. 7 shows a TEM image of a core/shell structured upconversion nanophosphor according to Example 4. Referring to the TEM image of the upconversion nanophosphor, it is seen that NaYF$_4$:Nd,Yb shell was formed around the core, thereby resulting in an increase in the size of a nanoparticle. Referring to a high-resolution TEM image thereof, it is seen that the synthesized upconversion nanophosphor having the core/shell structure has a hexagonal structure. Referring to the PL spectra of the upconversion nanophosphor having the core structure synthesized according Example 2 and the upconversion nanophosphor having the core/shell structure synthesized according Example 4 shown in FIG. 8, it is seen that when excited by infrared light having a wavelength of 800 nm, the core upconversion nanophosphor did not have an emission peak, and the core/shell structured upconversion nanophosphor had emission peaks. These results show that the Nd$^{3+}$ doped shell was formed around the core.

Figure 9:
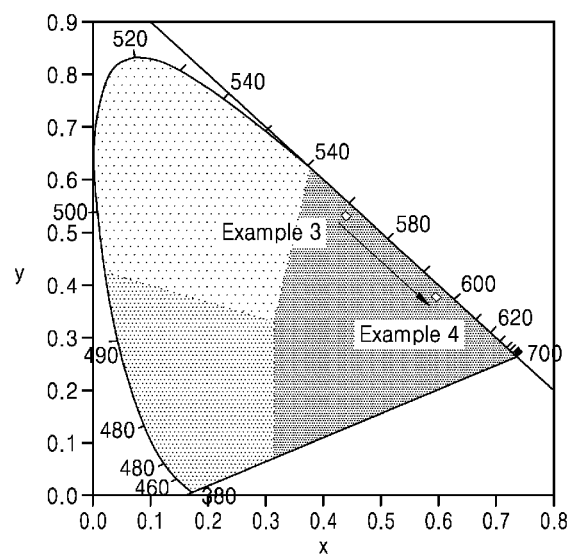
FIG. 9 shows a chromaticity diagram showing the color coordinates of a core/shell structured upconversion nanophosphor according to an embodiment of the present disclosure.

FIG. 9 shows a chromaticity diagram showing the color coordinates of the core/shell structured upconversion nanophosphors synthesized according to Examples 3 and 4. From the chromaticity diagram shown in FIG. 9, it is seen that the upconversion nanophosphors each having the core/shell structure synthesized according to embodiments of the present disclosure emit green light and red light when excited by infrared light having a wavelength of 800 nm.

<Example 5> Synthesis of Nd$^{3+}$ Doped Core/Shell Structured Red Light-Emitting Upconversion Nanophosphor Prepared was a core/shell structured nanophosphor including NaGd$_{0.5}$F$_4$:Yb$^{3+}$$_{0.18}$,Ho$^{3+}$$_{0.02}$,Ce$^{3+}$$_{0.3}$ nanoparticle prepared according to Example 2 as a core and a Nd$^{3+}$ and Yb$^{3+-}$doped NaGdF$_4$ fluoride-based compound as a shell.

0.45 mmol gadolinium chloride hexahydrate (GdCl$_3$.6H$_2$O), 0.5 mmol neodymium chloride hexahydrate (NdCl$_3$.6H$_2$O), and 0.05 mmol ytterbium chloride hexahydrate (YbCl$_3$. 6H$_2$O) were mixed with a solution including oleic acid and 1-octadecene, and the mixture was heat treated at a temperature of 150° C. for 30 minutes to prepare a first mixed solution containing a lanthanide complex (preparation of a first mixed solution).

The first mixed solution was mixed with a solution including NaGd$_{0.5}$F$_4$:Yb$^{3+}$$_{0.18}$,Ho$^{3+}$$_{0.02}$,Ce$^{3+}$$_{0.3}$ nanoparticle prepared according to Example 2 to prepare a second mixed solution.

10 ml of a methanol solution containing 2.5 mmol of sodium hydroxide and 4 mmol of ammonium fluoride was prepared (preparation of a third mixed solution), and then, the third mixed solution was mixed with the second mixed solution containing a lanthanide complex (preparation of reaction solution).

After the mixing is sufficiently performed, methanol was removed therefrom and the resultant solution was heat treated in an inert gas atmosphere. At this time, when the heat treatment temperature is lower than 200° C., a single hexagonal-phase nanocrystal is not completely formed and a phosphor does not exhibit strong luminescence. When the heat treatment temperature is higher than 370° C., aggregation of particles occurs due to excessive reaction, resulting in a very large particle size, a non-uniform distribution of the size, and a weak luminescence. Therefore, the heat treatment temperature may be in a range of about 200° C. to about 370° C. and the heat treatment time may be in a range of about 10 minutes to about 4 hours (preparation of nanoparticles). The resultant nanoparticles were cooled to room temperature after the heat treatment process, thereby obtaining a colloidal nanophosphor with a diameter of about 2 nm to about 60 nm. The prepared nanophosphor was washed with acetone or ethanol, and then, stored while being dispersed in a non-polar solvent such as hexane, toluene, or chloroform.

Figure 10:
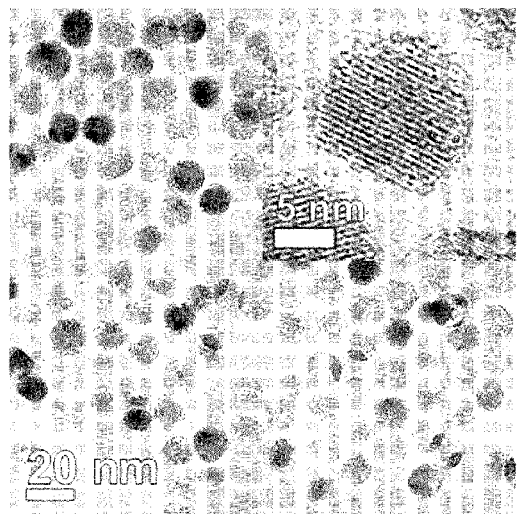
FIG. 10 shows a TEM image of a core/shell structured upconversion nanophosphor according to an embodiment of the present disclosure.
Figure 11:
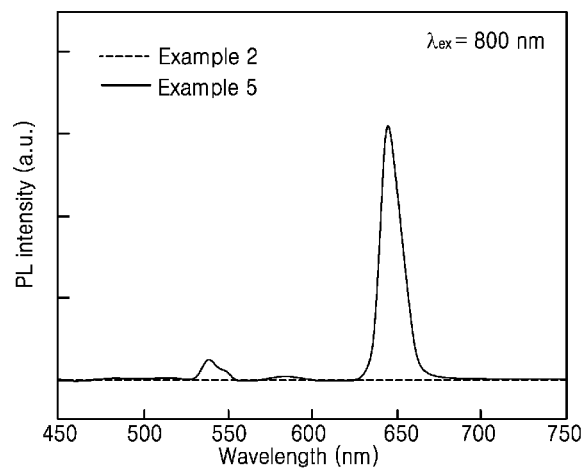
FIG. 11 shows PL spectra of a core/shell structured upconversion nanophosphor according to an embodiment of the present disclosure.

FIG. 10 shows a TEM image of a core/shell structured upconversion nanophosphor according to Example 5. Referring to the TEM image of the upconversion nanophosphor, it is seen that NaGdF$_4$:Nd,Yb shell was formed around the core, thereby resulting in an increase in the size of a nanoparticle. Referring to a high-resolution TEM image thereof, it is seen that the synthesized upconversion nanophosphor having the core/shell structure has a hexagonal structure. Referring to the PL spectra of the upconversion nanophosphor having the core structure synthesized according to Example 2 and the upconversion nanophosphor having the core/shell structure synthesized according to Example 5 shown in FIG. 11, it is seen that when the upconversion nanophosphor having the core/shell structure was excited by infrared light having a wavelength of 800 nm, a strong emission peak was observed in the red spectrum region. This result shows that a Nd$^{3+-}$doped NaGdF$_4$ shell is formed around the core.

<Example 6> Synthesis of Core/Shell/Shell Structured Red Light-Emitting Upconversion Nanophosphor Prepared was a core/shell/shell structured nanophosphor including NaGd$_{0.5}$F$_4$:Yb$^{3+}$$_{0.18}$,Ho$^{3+}$$_{0.02}$,Ce$^{3+}$$_{0.3}$/NaGdF$_4$:Nd$^{3+}$$_{0.5}$,Yb$^{3+}$$_{0.05}$ nanoparticle prepared according to Example 5 as a core and a NaGdF$_4$ fluoride-based compound as a shell.

1 mmol gadolinium chloride hexahydrate (GdCl$_3$.6H$_2$O) was mixed with a solution including oleic acid and 1-octadecene, and the mixture was heat treated at a temperature of 150° C. for 30 minutes to prepare a first mixed solution containing a lanthanide complex (preparation of first mixed solution).

The first mixed solution was mixed with the solution including a $NaGd_{0.5}F_4{:}Yb^{3+}{}_{0.18},Ho^{3+}{}_{0.02},Ce^{3+}{}_{0.3}/NaYF_4{:}Nd^{3+}{}_{0.5},Yb^{3+}{}_{0.05}$ nanoparticle prepared according to Example 5 to prepare a second mixed solution.

10 ml of a methanol solution containing 2.5 mmol of sodium hydroxide and 4 mmol of ammonium fluoride was prepared (preparation of third mixed solution), and then, the second mixed solution was mixed with a second-mixed solution containing a lanthanide complex (preparation of reaction solution).

After the mixing is sufficiently performed, methanol was removed therefrom and the resultant solution was heat treated in an inert gas atmosphere. At this time, when the heat treatment temperature is lower than 200° C., a single hexagonal-phase nanocrystal is not completely formed and a phosphor does not exhibit strong luminescence. When the heat treatment temperature is higher than 370° C., aggregation of particles occurs due to excessive reaction, resulting in a very large particle size, a non-uniform distribution of the size, and a weak luminescence. Therefore, the heat treatment temperature may be in a range of about 200° C. to 370° C. and the heat treatment time may be in a range of about 10 minutes to about 4 hours (Preparation of nanoparticles). The resultant nanoparticles were cooled followed by the heat treatment process, thereby obtaining colloidal nanophosphor having a diameter of about 3 nm to about 100 nm, for example, about 3 nm to about 50 nm. The prepared nanophosphor was washed with acetone or ethanol, and then, stored while being dispersed in a non-polar solvent such as hexane, toluene, or chloroform.

Figure 12:
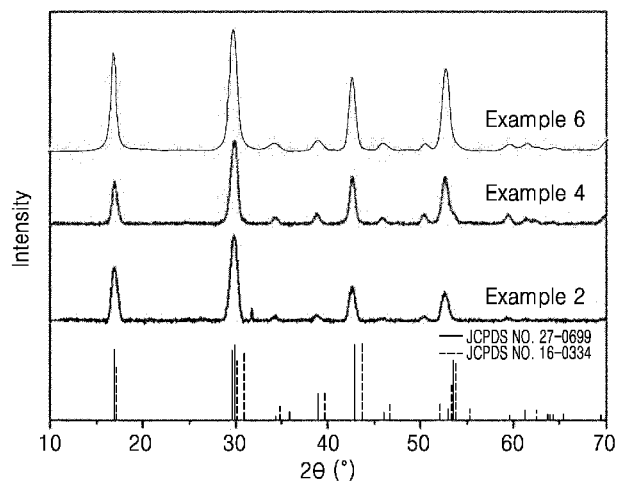
FIG. 12 shows X-ray diffraction patterns of an upconversion nanophosphor having a core structure, an upconversion nanophosphor having a core/shell structure, and an upconversion nanophosphor having a core/shell/shell structure, according to embodiments of the present disclosure.
Figure 13:
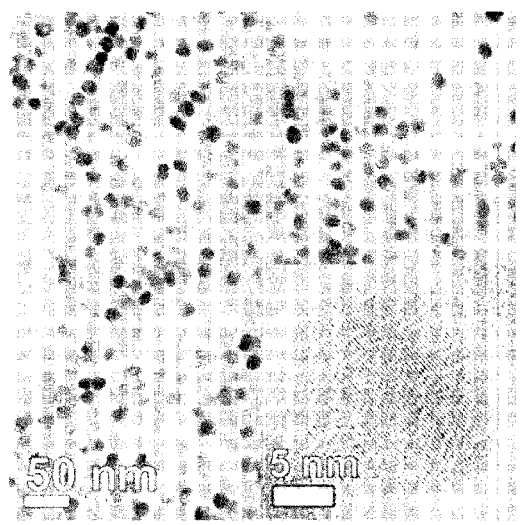
FIG. 13 shows a TEM image of a core/shell/shell structured upconversion nanophosphor according to an embodiment of the present disclosure.
Figure 14:
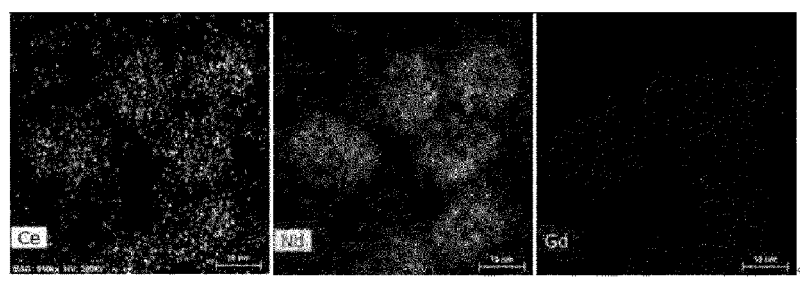
FIG. 14 shows a scanning transmission electron microscopy and energy dispersive X-ray spectroscopic image of the upconversion nanophosphor having the core/shell/shell structure according to an embodiment of the present disclosure.
Figure 15:
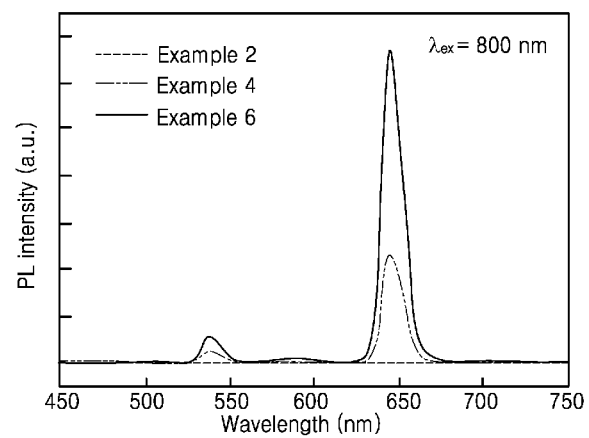
FIG. 15 shows PL spectra of an upconversion nanophosphor having a core structure, an upconversion nanophosphor having a core/shell structure, and an upconversion nanophosphor having a core/shell/shell structure, according to embodiments of the present disclosure.

Referring to the x-ray diffraction patterns shown in FIG. 12, it is seen that the upconversion nanophosphor having the core structure of Example 2, the upconversion nanophosphor having the core/shell structure of Example 4, and the upconversion nanophosphor having the core/shell/shell structure of Example 6 each have a hexagonal structure. FIG. 13 shows a TEM image of a core/shell/shell structured upconversion nanophosphor according to Example 6. Referring to the TEM image of the upconversion nanophosphor, it is seen that $NaGdF_4$ shell was formed around the core/shell nanophosphor, thereby resulting in an increase in the size of a nanoparticle. Referring to a high-resolution TEM image thereof, it is seen that the synthesized upconversion nanophosphor having the core/shell/shell structure has a hexagonal structure. Referring to the scanning transmission electron microscopy and energy dispersive X-ray spectroscopic image, it is seen that a first shell and a second shell are formed around the core. Referring to the PL spectra of FIG. 15, it is seen that when the second shell was formed around the core/shell structure, luminescence of the upconversion nanophosphor was greatly increased, and when the upconversion nanophosphor was excited by near infrared light having a wavelength of 800 nm, a strong emission peak appeared in the red light region.

<Example 7> Synthesis of Core/Shell/Shell Structured Red Light-Emitting Upconversion Nanophosphor Dispersible in Water Prepared was a core/shell/shell structured nanophosphor dispersible in water by modifying the surface of the core/shell/shell nanoparticle having a $NaGd_{0.5}F_4{:}Yb^{3+}{}_{0.18},$ $Ho^{3+}{}_{0.02},Ce^{3+}{}_{0.3}/NaGdF_4{:}Nd^{3+}{}_{0.5},Yb^{3+}{}_{0.05}/NaGdF_4$ structure prepared according to Example 6 by removing a ligand therefrom.

1 mL of a chloroform solution with the core/shell/shell structure nanophosphor prepared according to Example 6 dispersed therein was dispersed in 0.5 mL of 2 M hydrochloric acid solution, and then the mixture was sonicated for 5 minutes. The sonicated solution was centrifuged to isolate nanophosphor particles from which a ligand had been removed. The nanophosphor particles were washed with ethanol, and then, dispersed in water.

Figure 16:
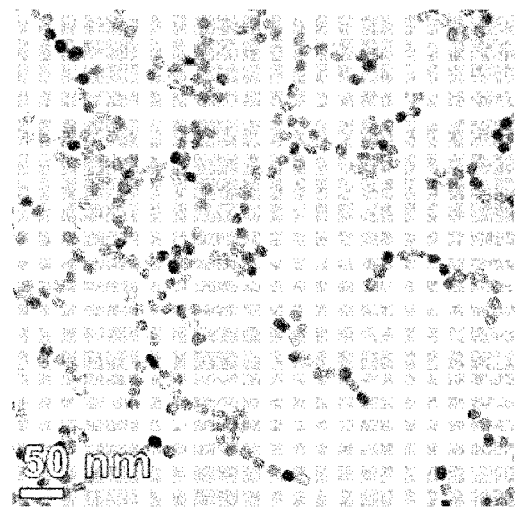
FIG. 16 shows a TEM image of a core/shell/shell structured upconversion nanophosphor, which is dispersible in water, according to an embodiment of the present disclosure.
Figure 17:
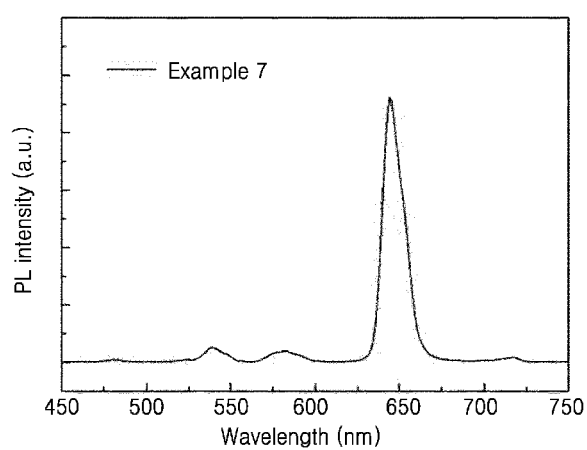
FIG. 17 shows a PL spectrum of an upconversion nanophosphor having a core/shell/shell structure, according to embodiments of the present disclosure.

FIG. 16 shows a TEM image of the nanophosphor particles from which the ligand has been removed according to Example 7. It is seen that the ligand-free nanophosphor is dispersed in a uniform size without aggregation. FIG. 17 shows a PL spectrum of the ligand-free core/shell/shell structured nanophosphor according to Example 7. As shown in the PL spectrum, when excited by infrared light having a wavelength of 800 nm, the nanophosphor showed a strong emission peak in a red spectrum region.

As described above, a core/double shell-structured inorganic nanophosphor according to embodiments of the present disclosure has upconversion luminescent characteristics, that is, an emission peak in a red spectrum region by absorbing infrared light having a wavelength of about 800 nm, has upconversion red emission enhanced by including a Gd-containing shell in its outmost shell and magnetic resonance imaging contrast characteristics.

When the inorganic nanophosphor according to the present disclosure is used as a fluorescent contrast agent, the temperature increase effect on the biotissue is small, the upconversion emission signal can be obtained from a part located deep in living tissues, and magnetic resonance imaging effects may be obtained. Accordingly, the inorganic nanophosphor may be suitable for, in addition to a contrast agent for bio-imaging, use in a disease diagnosis field. In addition, since the infrared light of two different wavelengths can be used as a light source, it is possible to improve the accuracy of fluorescence imaging.

Furthermore, due to the use of infrared light, the core/double shell structured upconversion nanophosphor according to the present disclosure is applicable to security related fields, for example, use as an anti-counterfeit code.

However, these effects are an example only and do not limit the scope of the present disclosure.

As described above, the present disclosure has been described with reference to embodiments of the present disclosure. However, those skilled in the art may understand that the present disclosure may be modified or changed in various ways without departing from the spirit and scope of the present disclosure set forth in the following claims. Those skilled in the art may make various changes in form and details in the technical concept of the present disclosure. The changes in form and details may be included inside the scope of the present disclosure as long as they are obvious to one of ordinary skill in the art.

What is claimed is:

1. A red light-emitting upconversion nanophosphor having a core/double shell structure, the red light-emitting upconversion nanophosphor comprising
 a upconversion core comprising a $Yb^{3+}$, $Ho^{3+}$, and $Ce^{3+}$ co-doped fluoride-based nanophosphor, the upconversion core represented by Formula 1;
 a first shell surrounding at least a portion of the upconversion core, and comprising a $Nd^{3+}$ and $Yb^{3+}$ co-doped fluoride-based crystalline composition represented by Formula 2; and a second shell surrounding at least a portion of the first shell, and having paramagnetic properties, represented by Formula 3:

$$NaGd_{1-x-y-z-w}L_wF_4:Yb^{3+}{}_x,Ho^{3+}{}_y,Ce^{3+}{}_z \quad \text{[Formula 1]}$$

wherein, in Formula 1, x is a real number and satisfies the condition of $0 \le x \le 0.5$, y is a real number and satisfies the condition of $0 < y \le 0.3$, and z is a real number and satisfies the condition of $0 < z \le 0.5$, and in this regard, x, y, and z satisfies the condition of $0 < x+y+z \le 1$, L is any one selected from Y, La, Tb, Dy, Er, Tm, Nd, Lu, and a combination thereof, and w is a real number and satisfies the conditions of $0 \le w \le 1$ and $0 < x+y+z+w \le 1$:

$$NaY_{1-p-q-r}M_rF_4:Nd^{3+}{}_p,Yb^{3+}{}_q \quad \text{[Formula 2]}$$

wherein, in Formula 2, p is a real number and satisfies the condition of $0 < p \le 1$, q is a real number and satisfies the condition of $0 \le q \le 0.5$, M is any one selected from first rare-earth elements and a combination thereof, the first rare-earth elements are selected from La, Ce, Gd, Pr, Sm, Eu, Tb, Dy, Er, and Lu, and r is a real number and satisfies the condition of $0 \le r \le 1$ and the condition of $0 < p+q+r \le 1$:

$$NaGd_{1-s}N_sF_4 \quad \text{[Formula 3]}$$

wherein N in Formula 3 is any one selected from second rare-earth elements and a combination thereof, the second rare-earth elements are selected from Y, La, Ce, Nd, Pr, Sm, Eu, Tb, Dy, Ho, Yb, Er, and Lu, and s satisfies the condition of $0 \le s \le 1$.

2. The red light-emitting upconversion nanophosphor of claim 1, wherein
the upconversion core represented by Formula 1 has a size of about 1 nm to about 20 nm.

3. The red light-emitting upconversion nanophosphor of claim 1, wherein
the red light-emitting upconversion nanophosphor having the core/double shell structure has a size of about 3 nm to about 50 nm.

4. The red light-emitting upconversion nanophosphor of claim 1, wherein
the red light-emitting upconversion nanophosphor having the core/double shell structure absorbs near infrared light having a wavelength of about 770 nm to about 870 nm and show red light luminescent characteristics.

5. The red light-emitting upconversion nanophosphor of claim 1, wherein
the red light-emitting upconversion nanophosphor having the core/double shell structure absorbs near infrared light having a wavelength of about 940 nm to about 1,000 nm and show red light luminescent characteristics.

6. A fluorescent contrast agent comprising the red light-emitting upconversion nanophosphor of claim 1.

7. A contrast agent for magnetic resonance imaging, the contrast agent comprising the red light-emitting upconversion nanophosphor of claim 1.

8. The red light-emitting upconversion nanophosphor of claim 1, wherein,
in Formula 2, p+q+r=1.

9. A red light-emitting upconversion nanophosphor having a core/double shell structure, the red light-emitting upconversion nanophosphor comprising:
an upconversion core comprising a $Yb^{3+}$, $Ho^{3+}$, and $Ce^{3+}$ co-doped fluoride-based nanophosphor, the upconversion core represented by Formula 1;
a first shell surrounding at least a portion of the upconversion core, and comprising a $Nd^{3+}$ and $Yb^{3+}$ co-doped fluoride-based crystalline composition represented by Formula 2a; and
a second shell surrounding at least a portion of the first shell, and having paramagnetic properties, represented by Formula 3:

$$NaGd_{1-x-y-z-w}L_wF_4:Yb^{3+}{}_x,Ho^{3+}{}_y,Ce^{3+}{}_z \quad \text{[Formula 1]}$$

wherein, in Formula 1, x is a real number and satisfies the condition of $0 \le x \le 0.5$, y is a real number and satisfies the condition of $0 < y \le 0.3$, and z is a real number and satisfies the condition of $0 \le z \le 0.5$, and in this regard, x, y, and z satisfy the condition of $0 < x+y+z \le 1$, L is any one selected from Y, La, Tb, Dy, Er, Tm, Nd, Lu, and a combination thereof, and w is a real number and satisfies the conditions of $0 \le w \le 1$ and $0 < x+y+z+w \le 1$:

$$NaM_eF_4:Nd^{3+}{}_p,Yb^{3+}{}_q \quad \text{[Formula 2a]}$$

wherein, in Formula 2a, p is a real number and satisfies the condition of $0 < p \le 1$, q is a real number and satisfies the condition of $0 \le q \le 0.5$, M is any one selected from first rare-earth elements and a combination thereof, the first rare-earth elements are selected from La, Ce, Gd, Pr, Sm, Eu, Tb, Dy, Ho, Er, and Lu, and r is a real number and satisfies the condition of $0 \le r \le 1$ and the condition of $p+q+r=1$:

$$NaGd_{1-s}N_sF_4 \quad \text{[Formula 3]}$$

wherein N in Formula 3 is any one selected from second rare-earth elements and a combination thereof, the second rare-earth elements are selected from Y, La, Ce, Nd, Pr, Sm, Eu, Tb, Dy, Ho, Yb, Er, and Lu, and s satisfies the condition of $0 \le s \le 1$.

* * * * *